United States Patent
Yao et al.

(10) Patent No.: US 11,384,182 B2
(45) Date of Patent: Jul. 12, 2022

(54) SUPRAMOLECULAR POLYMER COMPOSITION AND METHOD OF PREPARATION THEREOF

(71) Applicant: City University of Hong Kong, Kowloon (HK)

(72) Inventors: Xi Yao, Kowloon (HK); Gang Lu, Kowloon (HK)

(73) Assignee: City University of Hong Kong, Kowloon (HK)

(*) Notice: Subject to any disclaimer, the term of this patent is extended or adjusted under 35 U.S.C. 154(b) by 176 days.

(21) Appl. No.: 16/710,222

(22) Filed: Dec. 11, 2019

(65) Prior Publication Data

US 2021/0179749 A1 Jun. 17, 2021

(51) Int. Cl.
| | |
|---|---|
| A61K 47/08 | (2006.01) |
| A61K 47/44 | (2017.01) |
| A61P 31/00 | (2006.01) |
| C08F 210/02 | (2006.01) |
| A61K 45/06 | (2006.01) |

(52) U.S. Cl.
CPC ............ *C08F 210/02* (2013.01); *A61K 47/08* (2013.01); *A61K 47/44* (2013.01); *A61P 31/00* (2018.01); *A61K 45/06* (2013.01)

(58) Field of Classification Search
CPC ........ C08F 210/02; A61P 31/00; A61K 47/08; A61K 47/44; A61K 45/06
See application file for complete search history.

(56) References Cited

U.S. PATENT DOCUMENTS

| | | | |
|---|---|---|---|
| 6,280,751 B1 | 8/2001 | Fletcher et al. |
| 6,858,666 B2 | 2/2005 | Hamer et al. |
| 7,740,875 B2 | 6/2010 | Dechow |
| 8,138,157 B2 | 3/2012 | Rubsamen |
| 9,888,691 B2 | 2/2018 | Karandikar |
| 9,931,281 B2 | 4/2018 | Sun |
| 2009/0285869 A1 | 11/2009 | Trimble |
| 2018/0092780 A1 | 4/2018 | Eddy |

*Primary Examiner* — Alma Pipic
(74) *Attorney, Agent, or Firm* — Renner Kenner Greive Bobak Taylor & Weber

(57) ABSTRACT

A composition includes one or more monomeric units having a structure of Formula (I). The one or more monomeric units in the composition can encapsulate a hydrophobic material. Further, the invention provides a method of preparing said composition. The present invention also provides a method of killing or controlling the growth of microorganisms by contacting the microorganisms with said composition.

24 Claims, 15 Drawing Sheets

| | Maximum stress (MPa) | Maximum strain (mm/mm) | Young's modulus-tensile test (MPa) | Storage modulus G'-0.1 rad/s (MPa) | Young's modulus-indentation (MPa) | $T_g$ (°C) |
|---|---|---|---|---|---|---|
| $UP_1$-$C_0$ | 6.80±0.33 | 0.028±0.003 | 952.37±27.66 | 130.67±6.93 | 1440.76±87.53 | 90 |
| $UP_1$-$C_1$ | 3.66±0.25 | 0.10±0.01 | 99.83±2.77 | 70.38±2.43 | 840.55±32.84 | 82 |
| $UP_1$-$C_2$ | 2.67±0.14 | 0.22±0.02 | 42.16±1.32 | 16.52±0.45 | 320.32±8.65 | 60 |
| $UP_1$-$C_5$ | 0.80±0.03 | 0.45±0.04 | 7.98±0.23 | 0.12±0.01 | 45.26±1.43 | 9 |

FIG. 9

SUPRAMOLECULAR POLYMER COMPOSITION AND METHOD OF PREPARATION THEREOF

TECHNICAL FIELD

The present invention relates to a composition that includes one or more monomeric units that encapsulate a hydrophobic material. In particular, the monomeric units form a self-assembly polymer. The present invention also relates to a method of preparing a composition, and a method of killing or controlling the growth of microorganisms.

BACKGROUND OF INVENTION

Compositions that are capable of directional and reversible intermolecular self-assembly are of great interest and can be effective candidates for antimicrobial coatings due to their superior biocompatibility and antimicrobial capability. These compositions can be endowed with additional properties such as antimicrobial functions.

Currently, the most widely used inorganic antibacterial materials are silver nanoparticles (Ag NPs) and zinc oxide nanoparticles (ZnO NPs). However, these materials lack selectivity and can inhibit and kill pathogenic microbes as well as normal cells in the human body, qualities which are detrimental to, and limit, wide practical application. These materials also tend to inevitably suffer from damage during use, which reduces service life and increases costs remarkably.

Thus, self-healing compositions with advantageous qualities such as strong mechanical, antimicrobial and prolonged release properties are desired.

SUMMARY OF INVENTION

A first aspect of the present invention relates to a composition comprising one or more monomeric units having a structure of Formula (I), and wherein the one or more monomeric units encapsulate a hydrophobic material.

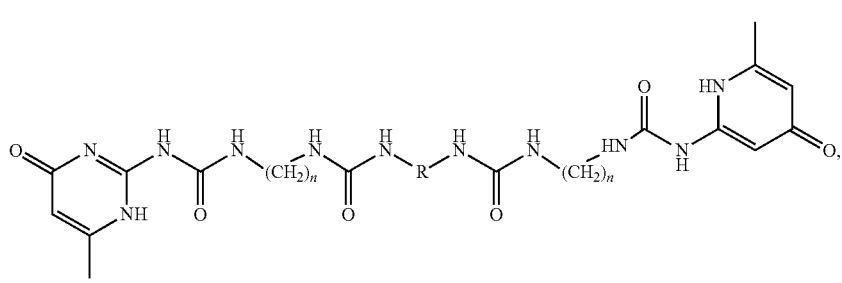

Formula (I)

in which:
n is an integer selected from 1 to 10;
R represents a substituted or unsubstituted cyclic group.

In an embodiment, the cyclic group is a 4, 5, 6, 7 or 8 membered aryl or heteroaryl group.

In one embodiment, the cyclic group is a 6 membered aryl group and R has a structure of Formula (IIa):

Formula (IIa)

in which:
$R_1$ and $R_2$ are independently selected from the group consisting of (i) a linear or branched alkyl group, optionally comprising a heteroatom; a linear or branched alkenyl group, optionally comprising a heteroatom; a linear or branched alkynyl group, optionally comprising a heteroatom; (ii) a cycloalkyl group optionally comprising a heteroatom; (iii) an aryl group, optionally comprising a heteroatom; and (iv) a heteroatom;

$R_3$, $R_4$, $R_5$ and $R_6$ are independently selected from the group consisting of (i) a linear or branched alkyl group, optionally comprising a heteroatom; a linear or branched alkenyl group, optionally comprising a heteroatom; a linear or branched alkynyl group, optionally comprising a heteroatom; (ii) a cycloalkyl group, optionally comprising a heteroatom; (iii) an aryl group, optionally comprising a heteroatom; (iv) a heteroatom; and (v) a hydrogen atom; and the dotted line denotes no double bonds, one double bond, two double bonds, or three double bonds in the cyclic group.

In another embodiment, R has a structure of Formula (IIb):

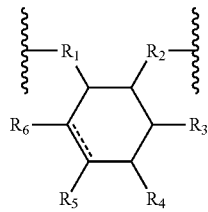

Formula (IIb)

in which:
R$_1$ and R$_2$ are independently selected from the group consisting of (i) a linear or branched alkyl group, optionally comprising a heteroatom; and (ii) a cycloalkyl group, optionally comprising a heteroatom;
R$_3$, R$_4$, R$_5$ and R$_6$ are independently selected from the group consisting of (i) a linear or branched alkyl group, optionally comprising a heteroatom, (ii) a heteroatom, and (iii) a hydrogen atom; and
the dotted line denotes no double bond or one double bond.

In a particular embodiment, R has a structure of Formula (IIb) with R$_1$, R$_2$, R$_3$ and R$_4$ being a linear or branched alkyl group, and R$_5$ and R$_6$ being a hydrogen atom.

In a further embodiment, the monomeric unit has a structure of Formula (III):

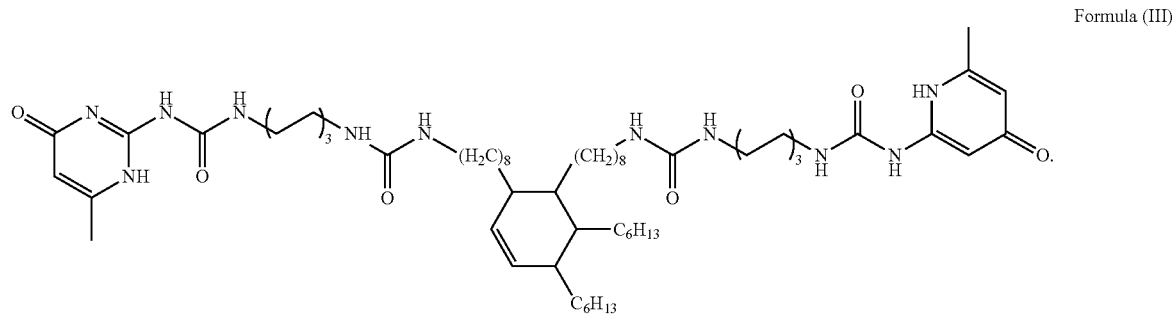

Formula (III)

The hydrophobic material, in an embodiment, is a liquid.

In an embodiment, the hydrophobic material comprises a pharmaceutically active ingredient. Preferably, the hydrophobic material comprises an antimicrobial compound.

In a preferred embodiment, the hydrophobic material is an essential oil. For example, the hydrophobic material comprises a compound selected from a group consisting of carvacrol, thymol, p-cymene, and limonene.

In an embodiment, the hydrophobic material disrupts bonding in the one or more monomeric units.

In another embodiment, the composition is a self-healing, sustained release antimicrobial.

Preferably, the composition has an elastic modulus of at least 50 MPa at 25° C. and of less than 5 MPa at 100° C.

A second aspect of the present invention relates to a method of preparing a composition, the method comprising the steps of (a) providing one or more monomeric units, the monomeric unit having a structure of Formula (I):

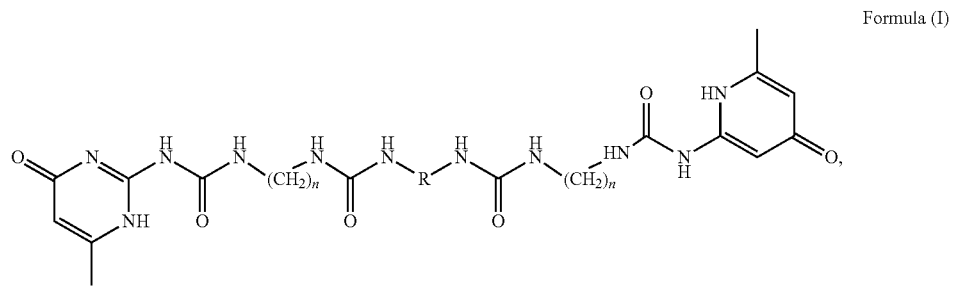

Formula (I)

in which:
n is an integer selected from 1 to 10;
R represents a substituted or unsubstituted cyclic group;

(b) mixing the one or more monomeric units with a hydrophobic material, and (c) obtaining the composition wherein the one or more monomeric units encapsulate the hydrophobic material.

In an example embodiment, step (b) is conducted by dissolving the one or more monomeric units in the hydrophobic material at a temperature of 50° C. to 150° C.

In one embodiment of the second aspect, R of Formula (I) has a structure of Formula (IIa):

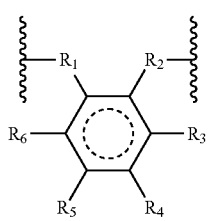

Formula (IIa)

in which:
$R_1$ and $R_2$ are independently selected from the group consisting of (i) a linear or branched alkyl group, optionally comprising a heteroatom; a linear or branched alkenyl group, optionally comprising a heteroatom; a linear or branched alkynyl group, optionally comprising a heteroatom; (ii) a cycloalkyl group optionally comprising a heteroatom; (iii) an aryl group, optionally comprising a heteroatom; and (iv) a heteroatom;

$R_3$, $R_4$, $R_5$ and $R_6$ are independently selected from the group consisting of (i) a linear or branched alkyl group, optionally comprising a heteroatom; a linear or branched alkenyl group, optionally comprising a heteroatom; a linear or branched alkynyl group, optionally comprising a heteroatom; (ii) a cycloalkyl group, optionally comprising a heteroatom; (iii) an aryl group, optionally comprising a heteroatom; (iv) a heteroatom; and (v) a hydrogen atom; and the dotted line denotes no double bonds, one double bond, two double bonds, or three double bonds in the cyclic group.

In a further embodiment, R of Formula (I) has a structure of Formula (IIb):

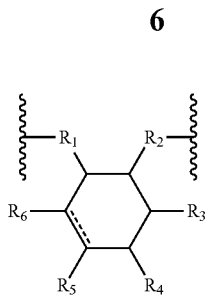

Formula (IIb)

in which:
$R_1$ and $R_2$ are independently selected from the group consisting of (i) a linear or branched alkyl group, optionally comprising a heteroatom; and (ii) a cycloalkyl group, optionally comprising a heteroatom;

$R_3$, $R_4$, $R_5$ and $R_6$ are independently selected from the group consisting of (i) a linear or branched alkyl group, optionally comprising a heteroatom; (ii) a heteroatom; and (iii) a hydrogen atom; and the dotted line denotes no double bond or one double bond.

Preferably, the monomeric unit in the step (a) is prepared by reacting a compound having Formula (IVa) and a compound having Formula (IVb):

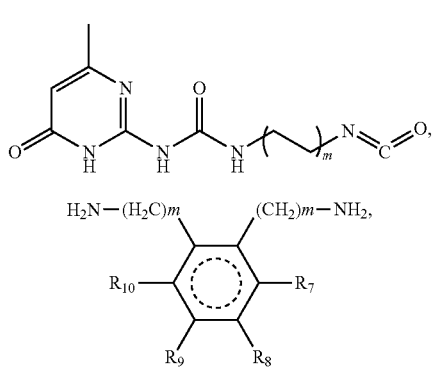

Formula (IVa)

Formula (IVb)

in which:
m is an integer selected from 1 to 10;
$R_7$, $R_8$, $R_9$, $R_{10}$ are independently selected from the group consisting of a linear or branched alkyl group, optionally comprising a heteroatom; a heteroatom; and a hydrogen atom; and
the dotted line denotes no double bonds, one double bond, two double bonds, or three double bonds in a cyclic group of Formula (IVb).

In another embodiment, the monomeric unit has a structure of Formula

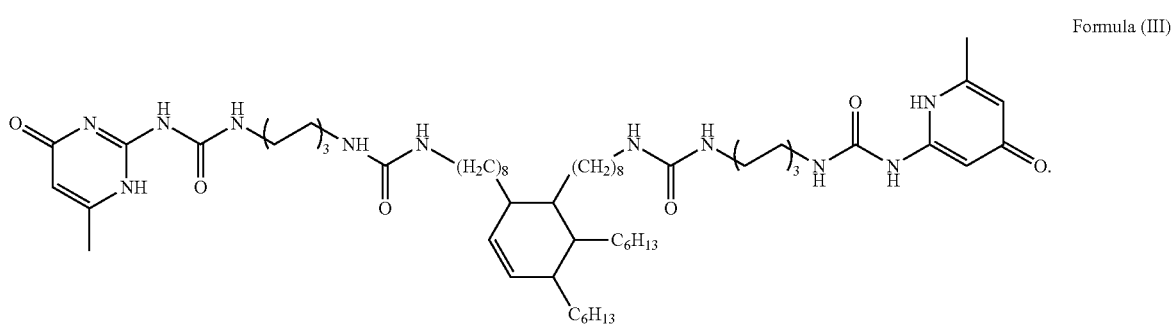

Formula (III)

In an embodiment, the hydrophobic material is a liquid.

In yet another embodiment, the hydrophobic material is an essential oil.

Preferably, the hydrophobic material comprises an antimicrobial compound. For example, a compound that kills or controls the growth of microorganisms such as, but not limited to, an antibacterial compound or an antifungal compound.

In an embodiment, the hydrophobic material comprises a compound selected from a group consisting of carvacrol, thymol, p-cymene, and limonene.

In a third aspect the present invention also pertains to a method of killing or controlling the growth of microorganisms comprising contacting the microorganisms with a composition as above. In particular, the microorganism is a bacterium.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF DRAWINGS

FIG. 9 is a table showing properties of the composition in accordance with an example embodiment.

DETAILED DESCRIPTION OF INVENTION

Figure 1:
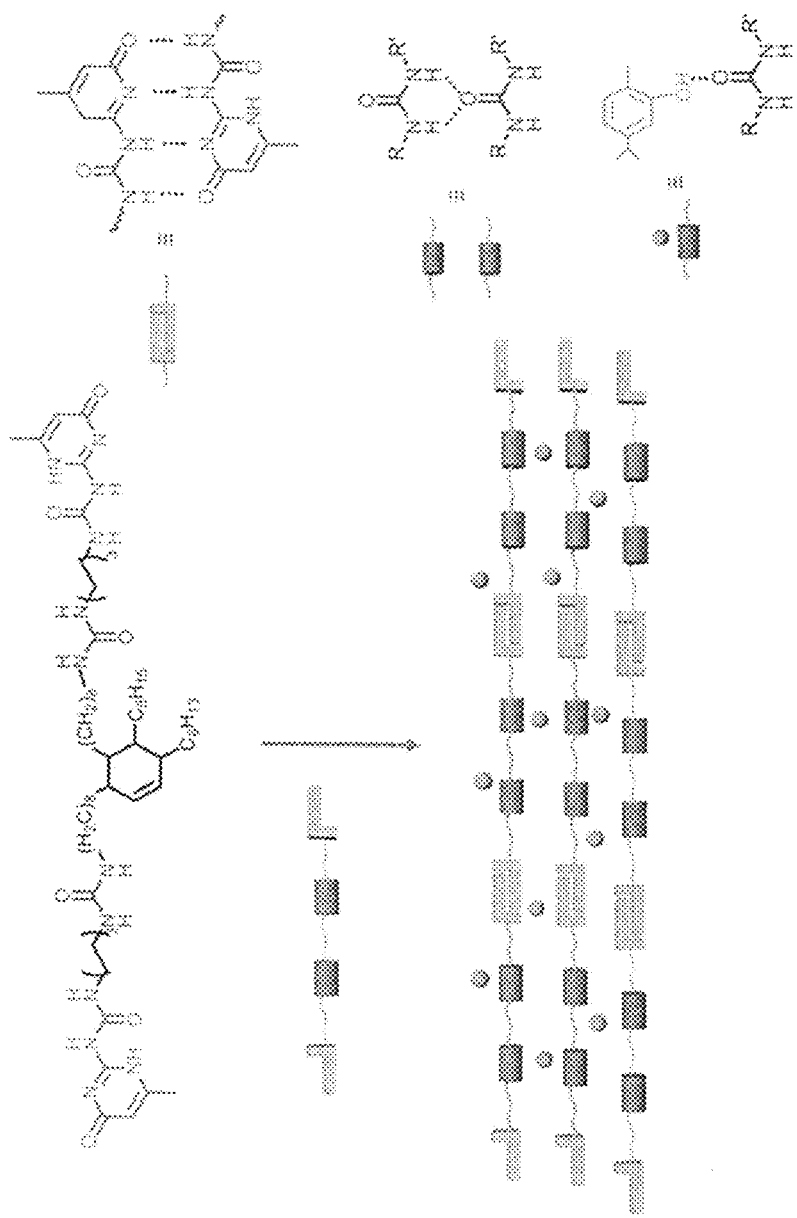
FIG. 1 is a schematic representation of the components of the composition, including the one or more monomeric units having a structure of Formula (I) and the hydrophobic material in accordance with an example embodiment.

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element.

The present invention provides a composition that includes one or more monomeric units. The monomeric unit has a structure of Formula (I):

Formula (I)

[Chemical structure of Formula (I)]

n is an integer selected from 1 to 10, R represents a substituted or unsubstituted cyclic group. The one or more monomeric units encapsulates a hydrophobic material.

n is an integer indicating the number of methylene bridges, i.e. —CH$_2$— groups, and is preferably selected from 1 to 5, more preferably selected from 1, 2, 3 or 4, further preferred from 2, 3 or 4 and in particular embodiments of the present invention, n is 3. For example, if n is 1, there is one methylene bridge present at the respective position.

In the context used herein, the one or more monomeric units can connect to each other to form a network or networks that define a core structure or backbone of the composition. The term "connect" encompasses any type of interaction which allows the formation of a network as described herein, and includes, without limitation, noncovalent bonding, for example, hydrogen bonds, metal-ligand interactions, pi interactions, ionic bonds, Van de Waals interactions, hydrophobic bonds, other reversible interactions and the like, and covalent bonding. In an example, the one or more monomeric units connect to each other via a host-guest interaction through non-covalent bonding that maintains the 3D structure of the one or more monomeric units. In an embodiment herein, the monomeric unit forms at least one hydrogen bond with adjacent monomeric unit, thereby forming a crosslinked network. In another example embodiment, the one or more monomeric units repeat continuously in a linear fashion to form a network. In yet another embodiment, the one or more monomeric units repeat in a branched fashion to form a network.

The term "monomeric unit" as used herein is a repeating unit whose repetition produces a polymer chain.

The term "supramolecular polymer" as used herein refers to polymers made up of monomeric units held together via non-covalent interactions, such as, but not limited to, hydrogen bonding.

As used herein, the term "cyclic group" refers to structures with one or more rings (i.e. cycloalkyls, cycloalkenyls, cycloalkynyls, aryls, heteroaryls, etc.) The rings may vary in size and can include all carbon atoms (carbocycles), no carbon atoms (inorganic cyclic groups), or carbons atoms and non-carbon atoms (heterocyclics). The cyclic group may be aromatic or non-aromatic.

The term "substituted" as used herein includes all substituents of compounds permissible in the context of the chemical rules of valence known to those of ordinary skill in the art. In some cases, substituted may generally refer to replacement of a hydrogen atom with a substituent as described herein. In a broad aspect, permissible substituents may include acyclic and cyclic, branched and unbranched, carbocyclic and heterocyclic, aromatic and non-aromatic substituents, and/or may include heteroatoms.

The term "hydrophobic material" as used herein relates to a material that repels water. Hydrophobic materials are generally non-polar. The hydrophobicity of a material may be determined by measuring water immiscibility and water solubility. Hydrophobic materials are generally water immiscible and insoluble in water. The hydrophobicity of a material, particularly solid materials, may also be determined by measuring water contact angles, i.e. wherein a liquid-vapour interface meets a solid surface. If a water contact angle on the solid surface is larger than 90 degrees, the solid surface is considered hydrophobic.

The hydrophobic material may be liquid and can include, for example, oils or fats. The hydrophobic material in the present invention may include ingredients such as, but not limited to, pharmaceutically active ingredients.

In an example embodiment, the cyclic group is a 4, 5, 6, 7 or 8 membered aryl or heteroaryl group.

In an embodiment, the cyclic group is a 6 membered aryl group and R has a structure of Formula (IIa):

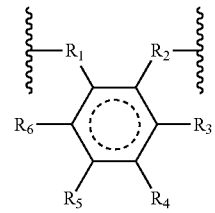

Formula (IIa).

$R_1$ and $R_2$ is independently selected from the group consisting of (i) a linear or branched alkyl group, optionally comprising a heteroatom; a linear or branched alkenyl group, optionally comprising a heteroatom; a linear or branched alkynyl group, optionally comprising a heteroatom; (ii) a cycloalkyl group optionally comprising a heteroatom; (iii) an aryl group, optionally comprising a heteroatom; and (iv) a heteroatom.

$R_3$, $R_4$, $R_5$ and $R_6$ is independently selected from the group consisting of (i) a linear or branched alkyl group, optionally comprising a heteroatom; a linear or branched alkenyl group, optionally comprising a heteroatom; a linear or branched alkynyl group, optionally comprising a heteroatom; (ii) a cycloalkyl group, optionally comprising a heteroatom; (iii) an aryl group, optionally comprising a heteroatom; (iv) a heteroatom; and (v) a hydrogen atom.

For example, the heteroatom may be selected from N, O, or S. The dotted line denotes no double bonds, one double bond, two double bonds or three double bonds in the cyclic group and the wavy line denotes a linkage between the R group and the adjacent atoms.

In a preferred embodiment, R has a structure of Formula (IIb):

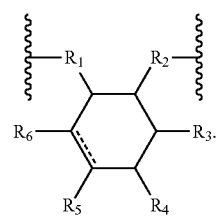

Formula (IIb)

$R_1$ and $R_2$ are independently selected from the group consisting of (i) a linear or branched alkyl group, optionally comprising a heteroatom; and (ii) a cycloalkyl group, optionally comprising a heteroatom. Preferably, $R_1$ and $R_2$ are a linear or branched alkyl group, further preferably a $C_5$-$C_{10}$-alkyl group. In particular embodiments of the present invention, $R_1$ and $R_2$ are a same linear $C_8$-alkyl group.

In an example embodiment, $R_3$, $R_4$, $R_5$ and $R_6$ may be independently selected from the group consisting of (i) a linear or branched alkyl group, optionally comprising a heteroatom, (ii) a heteroatom, and (iii) a hydrogen atom. In a preferred embodiment, $R_3$ and $R_4$ a linear or branched alkyl group, preferably a $C_1$-$C_{10}$-alkyl group, more preferably a $C_5$-$C_{10}$-alkyl group. Preferably $R_5$ and $R_6$ are a heteroatom or a hydrogen atom.

In an example embodiment, Formula (IIb) has no double bond. In an alternative embodiment, Formula (IIb) has a double bond.

In a particular embodiment of the present invention, Formula (IIb) has a double bond and $R_1$ and $R_2$ are the same unsubstituted $C_8$-alkyl group, $R_3$ is an unsubstituted $C_8$-alkyl group, $R_4$ is an unsubstituted $C_6$-alkyl group, and $R_5$ and $R_6$ are hydrogen atoms.

In a particular embodiment, the monomeric unit has a structure of Formula (III):

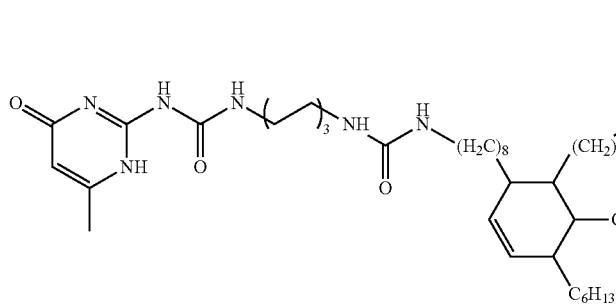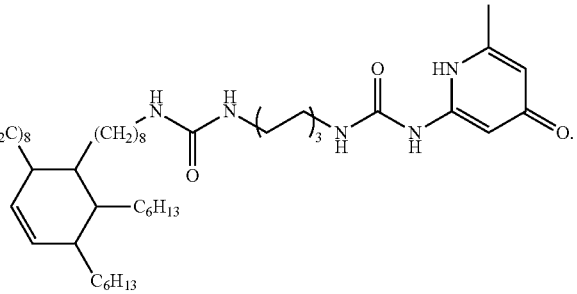

Formula (III)

In a preferred embodiment, the composition comprises one or more repeating monomeric units having a structure of Formula (III) that form a network or core structure of the composition. In one embodiment, the monomeric units repeat in a linear chain to form a network. In another embodiment, the monomeric units repeat in a branched fashion to form a network. In a particular embodiment, the monomeric units consist of a dimer diamine end-capped with ureidopyrimidinone (UPy). A monomeric unit may comprise one or more UPy motifs. In one example embodiment, the one or more monomeric units repeat continuously in a linear chain and the UPy motifs in the monomeric unit crosslink the linear chains to form a network. Preferably, the monomeric unit has two UPy motifs. In an alternative embodiment, the monomeric unit comprises at least three UPy motifs and wherein one or more monomeric units repeat to form a branched chain network.

The one or more monomeric units connect to form a core structure of the composition through polymerization and intermolecular crosslinks, whereby hydrogen bonding between the crosslinked network of the one or more monomeric units advantageously provide the core structure with high mechanical strength. The inventors found that ureidopyrimidinone end-caps form strong quadruple hydrogen bonds that promote chain extension, particularly linear chain extension, and facilitate monomeric properties, and weaker hydrogen bonds between the urea, i.e. $NH_2CONH_2$, also provide intermolecular crosslinks between the one or more monomeric unit backbone. The inventors also found that the ureidopyrimidinone end-caps of the monomeric units can be associated and disassociated under certain stimuli that advantageously provide the composition with self-assembly and self-healing properties when damaged.

The intermolecular crosslinks or connections between the monomeric units result in a composition with high mechanical strength and fast healing properties. A hydrophobic material is encapsulated in the one or more monomeric units. The term "encapsulate" means a material or compound is surrounded or partially surrounded by another material, i.e. the monomeric units herein. The encapsulated hydrophobic material may react with the one or more monomeric units and form non-covalent bond, i.e. being stably carried by the monomeric units.

In an embodiment, the hydrophobic material is a liquid. For example, the hydrophobic material is a hydrophobic liquid comprising volatile aromatic compounds. The volatile aromatic compounds can be released to the surrounding upon application of the composition.

In an example embodiment, the hydrophobic material includes an antimicrobial compound. The antimicrobial compound may include, but is not limited to, an antibacterial, an antifungal, an antiviral, or an antiparasitic. For example, the composition of the present invention may be applied as an antimicrobial coating for the prevention or treatment of clinical skin and wound infections, such as infections caused by gram-positive bacteria and/or gram-negative bacteria.

In a further embodiment, the hydrophobic material includes a pharmaceutically active ingredient and the composition can be used to prepare a sustained release dosage form for various medical purposes.

The hydrophobic material may comprise non-pharmaceutical ingredients such as, for example, an essential oil or anti-microbial pesticide. The hydrophobic material, in yet another embodiment, may include compounds derived from nature, such as plants. The compounds may be bioactive compounds extracted from, or synthesized from, different plants. In a preferred embodiment, the hydrophobic material is an essential oil. Preferably, the hydrophobic material includes a compound selected from a group consisting of carvacrol, thymol, p-cymene and limonene, or a mixture of two or more of these compounds. In a particular embodiment, the hydrophobic material comprises carvacrol and thymol. In a further preferred embodiment, the hydrophobic material includes carvacrol. For example, carvacrol has properties such as water immiscibility with a saturation concentration of carvacrol oil in water of about 3 mM.

In a particular embodiment, the hydrophobic material encapsulated in the one or more monomeric units includes an essential oil. An essential oil is a concentrated hydrophobic material comprising volatile chemical compounds. The essential oil has an aromatic structure and different functional groups that exhibit distinct chemical effects with the one or more monomeric units. Particularly, the inventors have found that varying the amount of essential oil in the composition can vary the mechanical strength of the composition and the hydrophobic material, particularly the essential oil, affect the mechanical strength by disrupting weak hydrogen bond crosslinks. Thus, the hydrophobic material disrupts bonding in the monomeric units while at the same time forms non-covalent linkage with the monomeric units. Accordingly, the content of essential oil in the composition can be used to control or regulate the mechanical properties of the composition and promote the formation of a gel-like consistency.

The inventors tested the effects of varying the amount of essential oil in the composition by preparing samples with different weight ratios of monomeric unit: essential oil, i.e. initial weight ratio of monomeric unit to essential oil of 1 to 0 ($UP_1$-$C_0$), initial weight ratio of monomeric unit to essential oil of 1 to 1 ($UP_1$-$C_1$), initial weight ratio of monomeric unit to essential oil of 1 to 2 ($UP_1$-$C_2$), and initial weight ratio of monomeric unit to essential oil of 1 to 5 ($UP_1$-$C_5$). The mechanical properties of the composition with varied amounts of essential oil were analysed using mechanical tensile-stress tests. The inventors conducted dynamic mechanical analysis (DMA) and determined that the composition had an elastic modulus range of 50 MPa to 500 MPa at 25° C. In a particular embodiment, the composition has an A disk diffusion assay was conducted to test the antimicrobial activity of the composition on gram-positive bacteria and gram-negative bacteria. Compared to the control sample, the composition comprising the monomeric unit and essential oil advantageously exhibited anti-bacterial ability in the presence of gram-negative and gram-positive bacteria. The bactericidal ability of the composition also correlated positively with the content of essential oil in the composition, i.e. a higher weight ratio of essential oil in the composition resulted in greater bactericidal ability. Thus, the composition of the present invention can be prepared as a structurally-robust, self-healing sustained release antimicrobial.

In another aspect, the present invention also refers to a method of preparing a composition, particularly the composition as described previously. The method comprises the steps of (a) providing one or more monomeric units having a structure of Formula (I):

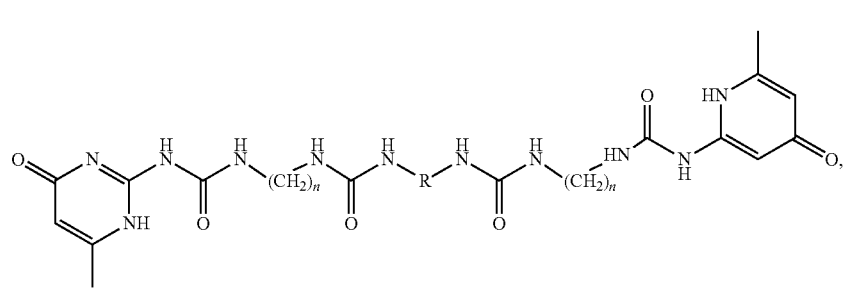

Formula (I)

elastic modulus of at least 50 MPa at 25° C. and of less than 5 MPa at 100° C. In a preferred embodiment, the composition has an elastic modulus of 50-150 MPa at 25° C. and of less than 3 MPa at 100° C. In a most preferred embodiment, the composition has an elastic modulus of 110 MPa at 25° C. and 0.6 MPa at 100° C.

The inventors also unexpectedly found that the hydrophobic material provided the composition with sustained release properties. The sustained release properties of the composition was analysed by comparing the amount of release of the hydrophobic material, particularly essential oil, in the composition compared to pure essential oil by calculating the change in mass (%) over time. Compared to pure essential oil which had approximately 40% reduction of the original mass at 100 days, the release amount from the composition of the present invention was found to be much lower, with a mass of 85-90% left at 100 days, demonstrating long-term stability of the composition in air. Release of essential oil in water was also investigated and the cumulative release of essential oil from the composition could last for up to 60 days (approximately 30% to 45% cumulative release), advantageously demonstrating controlled release properties of essential oil when encapsulated into the composition of the present invention.

The inventors also found that the composition showed self-healing properties by conducting healable tests. The composition showed increased self-healing efficiency with prolonged healing times, i.e. approximately 20% healing efficiency at 10 minutes to 95% healing efficiency at 40 minutes, and heating to 70° C. significantly accelerated the healing process. The healing efficiency of the composition at 40 minutes was 95.6% relative to a pristine sample, suggesting the beneficial self-healing capabilities of the composition.

in which:

n is an integer selected from 1 to 10;

R represents a substituted or unsubstituted cyclic group;

(b) mixing the one or more monomeric units with a hydrophobic material; and (c) obtaining the composition wherein the one or more monomeric units encapsulates the hydrophobic material.

Preferably, step (b) is conducted by dissolving the one or more monomeric units in the hydrophobic material at a temperature of 50 to 150° C.

In an example embodiment, the one or more monomeric units in the step (a) are prepared by reacting a compound having Formula (IVa) and a compound having Formula (IVb):

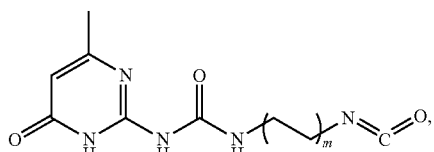

Formula (IVa)

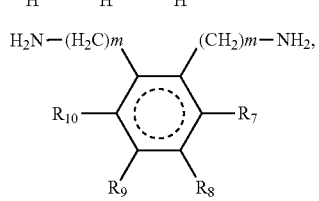

Formula (IVb)

in which:
  m is an integer selected from 1 to 10;
  $R_7$, $R_8$, $R_9$, $R_{10}$ are independently selected from the group consisting of a linear or branched alkyl group, optionally comprising a heteroatom; a heteroatom; and a hydrogen atom; and
  the dotted line denotes no double bonds, one double bond, two double bonds, or three double bonds in a cyclic group of Formula (IVb).

In a preferred embodiment, m is selected from 1 to 5, and $R_7$ and $R_8$ are a linear or branched alkyl group, preferably a $C_1$-$C_{10}$-alkyl group, more preferably a $C_5$-$C_{10}$-alkyl group. Preferably $R_9$ and $R_{10}$ are a heteroatom or a hydrogen atom.

In a further preferred embodiment of the present invention, Formula (IVb) has one double bond and $R_7$ is an unsubstituted $C_8$-alkyl group, $R_8$ is an unsubstituted $C_6$-alkyl group, and $R_9$ and $R_{10}$ are hydrogen atoms.

In a particular embodiment, the monomeric unit has a structure of Formula (III):

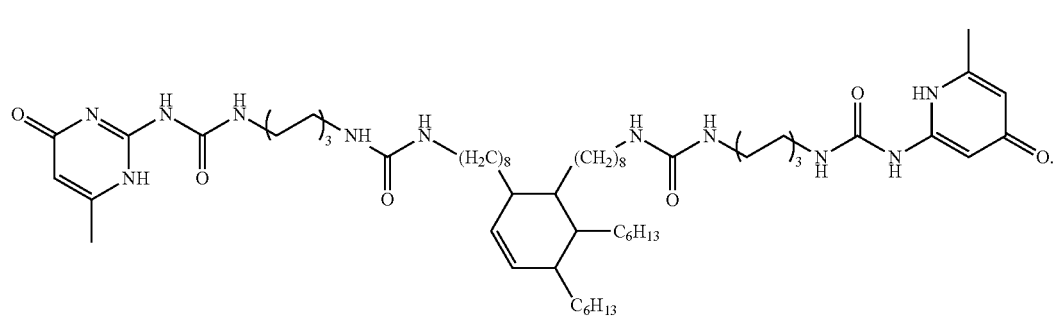

Formula (III)

In yet a further aspect, the present invention also refers to a method of killing or controlling the growth of microorganisms comprising contacting the microorganisms with a composition, particularly the composition as discussed previously.

It would be appreciated that the present invention also pertains to a kit comprising the composition as described above as well as use of the composition for medical purposes such as topical administration.

EXAMPLES

Example 1A

Molecular Design of the Composition

The claimed invention relates, in one aspect, to a composition comprising one or more monomeric units encapsulating a hydrophobic material. In one embodiment, the monomeric unit consists of a dimer diamine end-capped with ureidopyrimidinone (UPy). The inventors unexpectedly found that the composition of the present invention can be constructed through polymerization and intermolecular crosslinks, wherein a hierarchical hydrogen-bond crosslinked network can facilitate the composition with high mechanical strength and fast healing properties.

Ureidopyrimidinone motifs were found to form strong quadruple hydrogen bonds that promote linear chain extension and advantageously enable monomeric properties. Weak hydrogen bond interactions between urea units were found to provide intermolecular crosslinks between the monomeric backbones. The introduction of a hydrophobic material, for example carvacrol, into the one or more monomeric unit network disrupted the weak hydrogen bond crosslinks and facilitated the formation of a gel-like composition. The inventors beneficially found that the content of hydrophobic material, particularly carvacrol in this example, could be controlled to regulate the mechanical strength of the composition.

FIG. 1 illustrates the monomeric unit in accordance with an example embodiment. The monomeric unit is end-capped by a ureidopyrimidinone dimer (shown in L-shaped blocks), which is associated and dissociated under certain stimuli, enabling self-healing of the composition when damaged and directional and reversible intermolecular self-assembly. Strong quadruple bond hydrogen bonding between the ureidopyrimidinone is represented by the L-shaped blocks, weak hydrogen bonding interactions between urea motifs in the one or more monomeric units is shown in cylindrical blocks, and hydrophobic material molecules, particularly carvacrol oil molecules in a one embodiment, is shown in spherical blocks. The arrow illustrates the advantageous self-assembly of the one or more monomeric units and hydrophobic material form the composition.

Example 1B

Materials and Methods

Materials

Dimer diamines (Priamine 1074) were purchased from CRODA Coatings & Polymers. 2-amino-4-hydroxy-6-methylpyrimidine 99% was purchased from Acros Organics. Other chemicals and solvents were obtained from Sigma-Aldrich and used as received.

Synthesis of the Monomeric Unit of Formula (I)

In a particular embodiment, the monomeric unit has a structure of Formula (III), i.e. (UPy-NCO)$_2$Priamine. (UPy-NCO)$_2$Priamine was obtained by reacting 2 equivalents of UPy-NCO and 1 equivalent of priamine 1074. A 500-mL round bottom flask equipped with a reflux cooler was charged with priamine 1074 (1.593 g, 3 mmol) and DMSO (150 mL), then UPy-NCO (1.758 g, 6 mmol) was added drop wise. After reacting at 90° C. under the protection of nitrogen for 6 hours, the solvent DMSO was removed, and the solid product was washed 3 times with 60 mL portions of acetone. (UPy-NCO)$_2$Priamine was then collected by centrifugation and dried overnight under high vacuum at 60° C.

Preparation of Composition of the Present Invention 1 equivalent of (UPy-NCO)$_2$Priamine powder was stirred and dissolved in 2 equivalent carvacrol at 80° C. and evaporated at room temperature for 12 hours to promote full network formation. Preparation of compositions with different weight ratios of monomeric units and hydrophobic material were prepared according to the method described above and are summarised in Table 1 below. UP denotes monomeric unit (UPy-NCO)$_2$Priamine, C denotes hydrophobic material, particularly essential oil.

TABLE 1

Weight ratio of different samples of the composition of the present invention

| Composition | Weight Ratio (UP:C) |
|---|---|
| $UP_1$-$C_0$ | 1:0 |
| $UP_1$-$C_1$ | 1:1 |
| $UP_1$-$C_2$ | 1:2 |
| $UP_1$-$C_5$ | 1:5 |

Example 1C

Mechanical and Self-Healing Analysis

For mechanical tensile-stress and self-healing tests, sample size of 30 mm length×6 mm width×3 mm height, gauge length of 10 mm, and strain rate of 10 mm/min were adopted.

The tests were repeated at least three times and the average values were recorded. Dynamic mechanical analysis (DMA) was conducted on TA instruments (Q800 DMA). For self-healing tests, the polymer film was cut into two pieces and then put together. Healing tests on various samples can be conducted at different conditions. The healed samples followed the same procedure to obtain the tensile stress-strain curves. Rheology tests of gels were carried out by using Malvern Kinexus Lab$^+$ implemented with a 20-mm diameter parallel plate. The gap in the setup for rheological testing of the gels was 1.0 mm. Frequency sweeps were performed from 0.01 rad/s to 100 rad/s. Temperature sweeps were conducted from 20° C. to 100° C.

Figure 2:
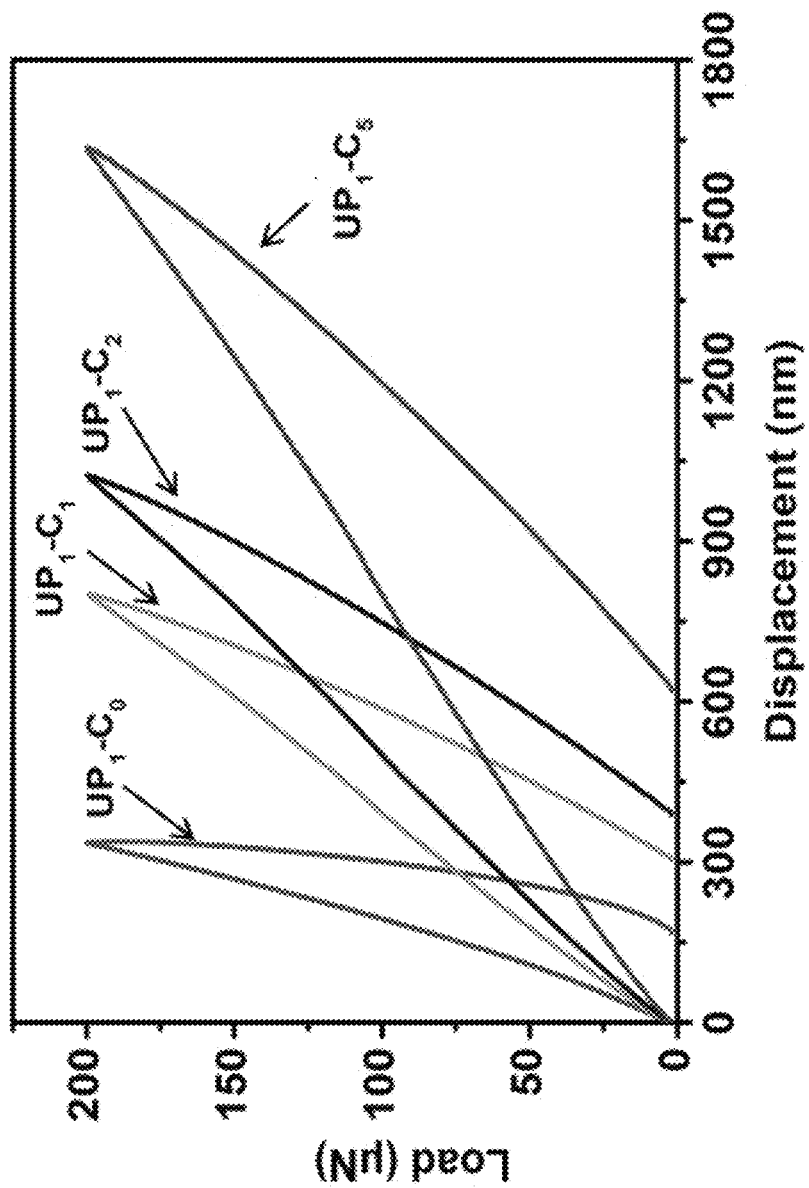
FIG. 2 shows indentation curves for nano-indentation tests conducted for the composition in accordance with an example embodiment.

FIG. 2 shows the results of a nano-indentation test to test the mechanical tensile-stress of samples of the composition. For $UP_1$-$C_0$, i.e. composition comprising a weight ratio of 1 monomeric unit to 0 hydrophobic material, particularly carvacrol, a Young's moduli 1.44 GPa reflected a very high stiffness. Young's modulus decreased as the content of carvacrol in the composition increased. This was illustrated in the results of the nano-indentation test whereby composition $UP_1$-$C_1$ had an elastic modulus of 420 MPa, composition $UP_1$-$C_2$ had an elastic modulus of 210 MPa, and composition $UP_1$-$C_5$ had an elastic modulus of 85 MPa.

Figure 3:
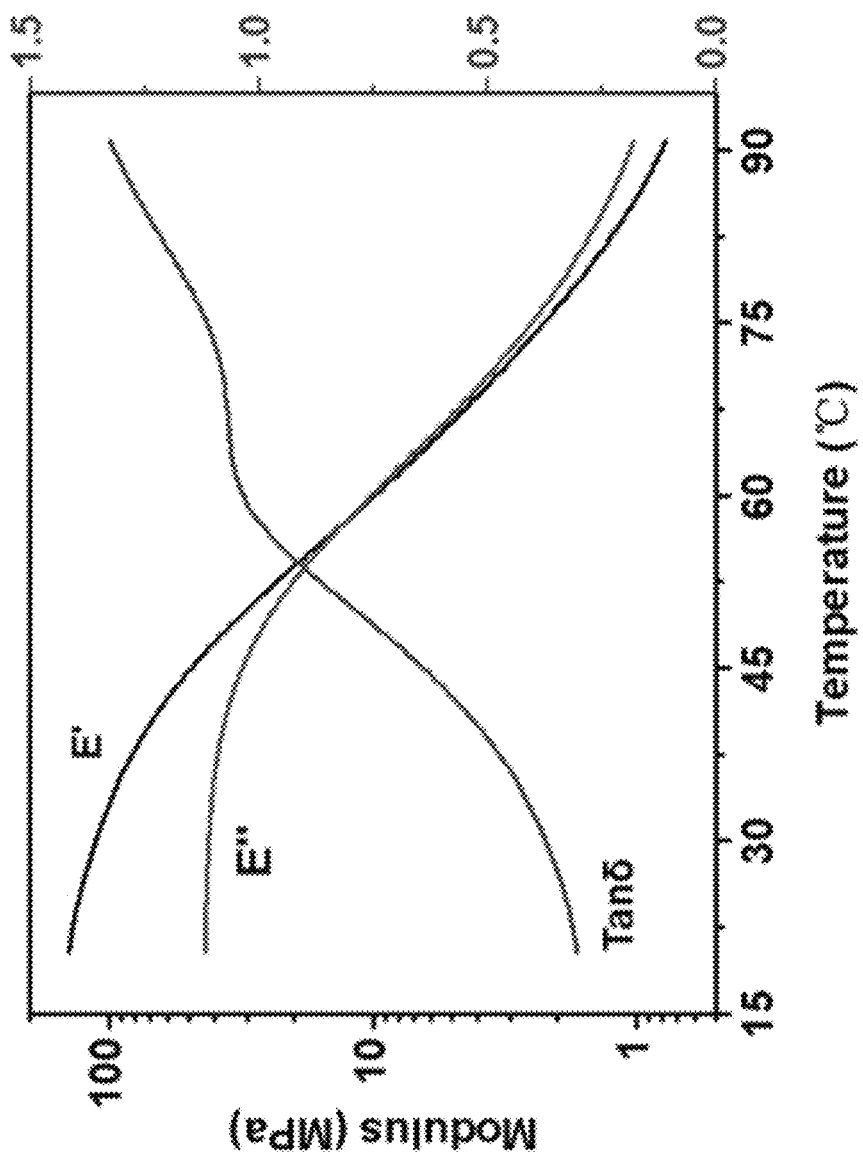
FIG. 3 shows a dynamic mechanical analysis of the composition in accordance with an example embodiment.

Further, with reference to FIG. 3, for composition $UP_1$-$C_2$, temperature-dependent dynamic mechanical analysis (DMA) analysis showed that the elastic modulus dropped rapidly from 110 MPa at room temperature to 0.9 MPa at 100° C., showing that the composition exhibits high strength at room temperature and exhibits healable characteristics at temperatures higher than 60° C.

Figure 4A:
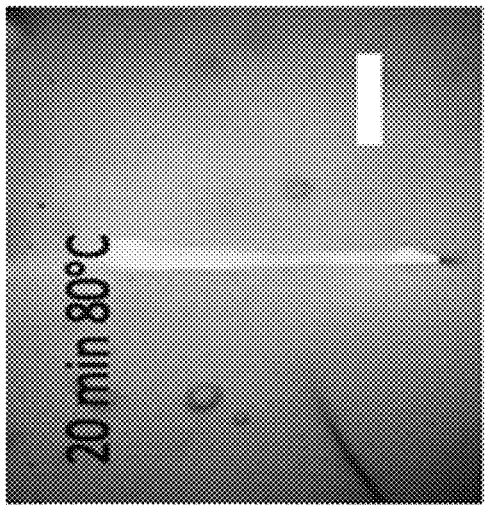
FIG. 4A is an in situ microscope photograph of the composition in accordance with an example embodiment.
Figure 4B:
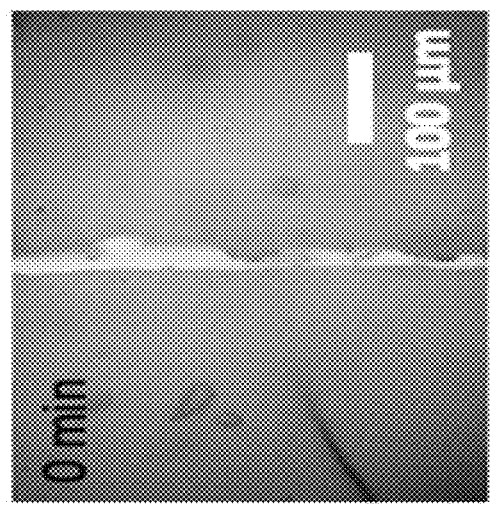
FIG. 4B is an in situ microscope photograph of the composition in accordance with an example embodiment.
Figure 4C:
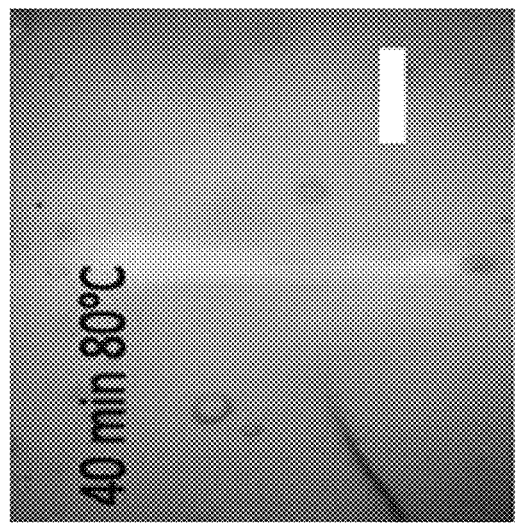
FIG. 4C is an in situ microscope photograph of the composition in accordance with an example embodiment.

FIG. 4A, FIG. 4B, FIG. 4C, FIG. 5 and FIG. 6 show the results of healable tests performed on composition sample $UP_1$-$C_2$. The sample was cut into two separate pieces with a razor blade and then placed in contact with hands. FIGS. 4A-4C illustrate in-situ microscope photographs of the $UP_1$-$C_2$ sample at different time points. FIGS. 4B and 4C show the sample at 20 minutes and 40 minutes, respectively, at 80° C. The results show that the self-healing efficiency of the composition increases with time. Heating the composition to 70° C. also significantly accelerates the healing process, which correlates with the rheological and DMA analysis showing that the modulus of the composition decreases above this temperature.

Figure 5:
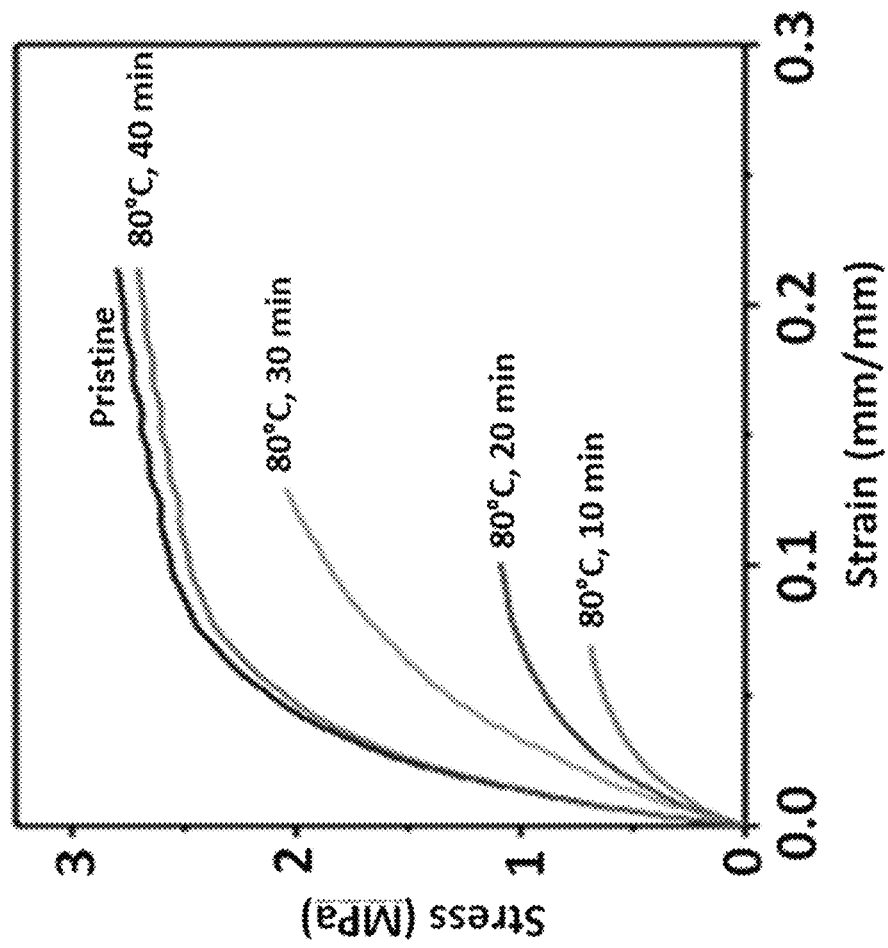
FIG. 5 is a line graph showing a tensile test of the composition with different healing times in accordance with an example embodiment.
Figure 6:
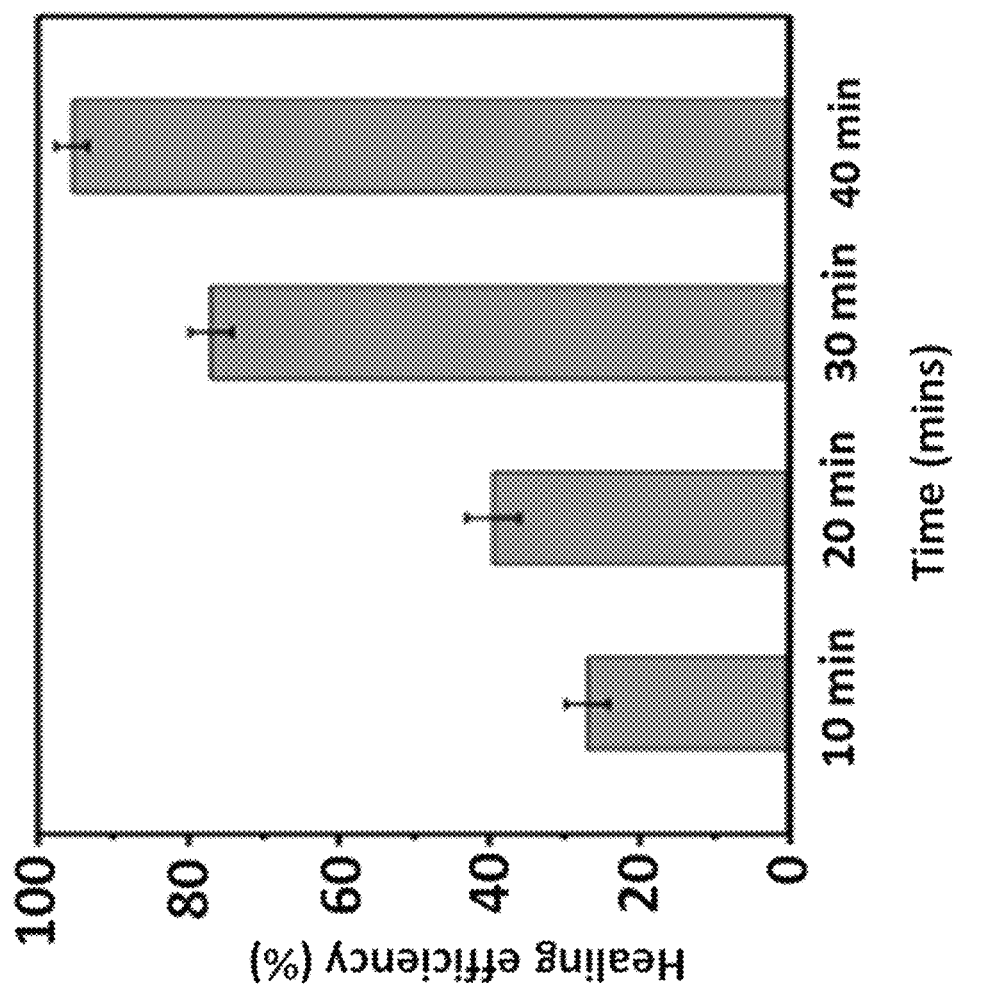
FIG. 6 is a bar graph showing healing efficiency of the composition at different time points in accordance with an example embodiment.

A tensile test on the composition testing different healing times was also conducted and is illustrated in FIG. 5 and FIG. 6. The healing efficiency of the sample at 40 minutes was 96.5% relative to pristine sample, potentially attributable to the chain motion and dynamic hydrogen bonding association.

FIG. 9 is a table showing properties of samples of the composition with different amounts of hydrophobic material, i.e. $UP_1$-$C_0$, $UP_1$-$C_1$, $UP_1$-$C_5$. The mechanical properties of the composition samples studied include maximum stress, maximum strain, Young's modulus-tensile test, storage modulus G'-0.1 rad/s, Young's modulus-indentation, and glass transition temperature ($T_g$).

Figure 10:
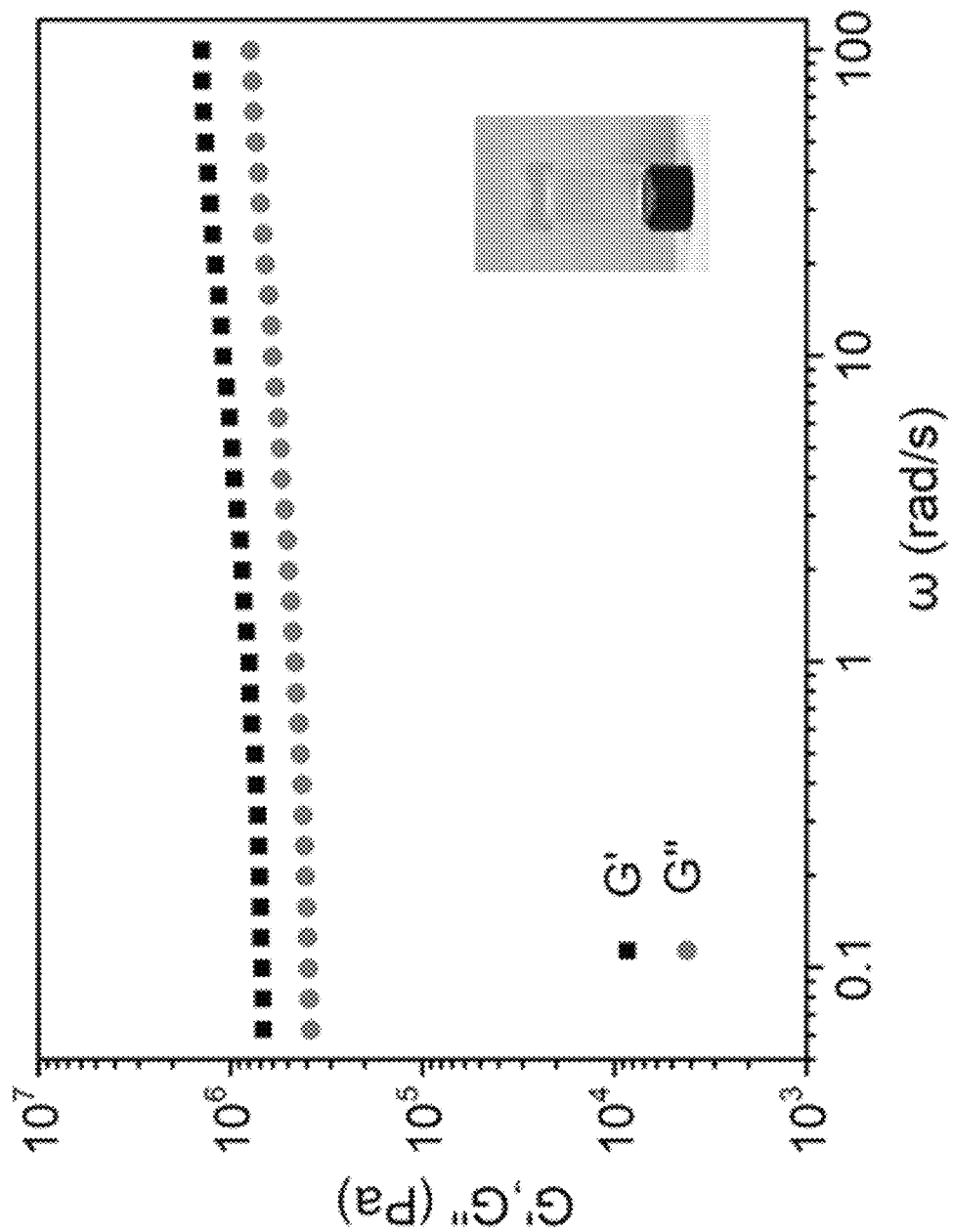
FIG. 10 is a scatter diagram showing the frequency sweep in rheology measurement of the monomeric unit in thymol in accordance with an example embodiment.

FIG. 10 is a scatter diagram showing the frequency sweep in rheology measurement for monomeric units assembled in thymol oil. Over the entire range of frequencies storage modulus (G') is higher than loss modulus (G"), illustrating solid-like properties. FIG. 10 also advantageously shows thymol oil as an effective hydrophobic material for encapsulation in the one or more monomeric units.

Figure 11:
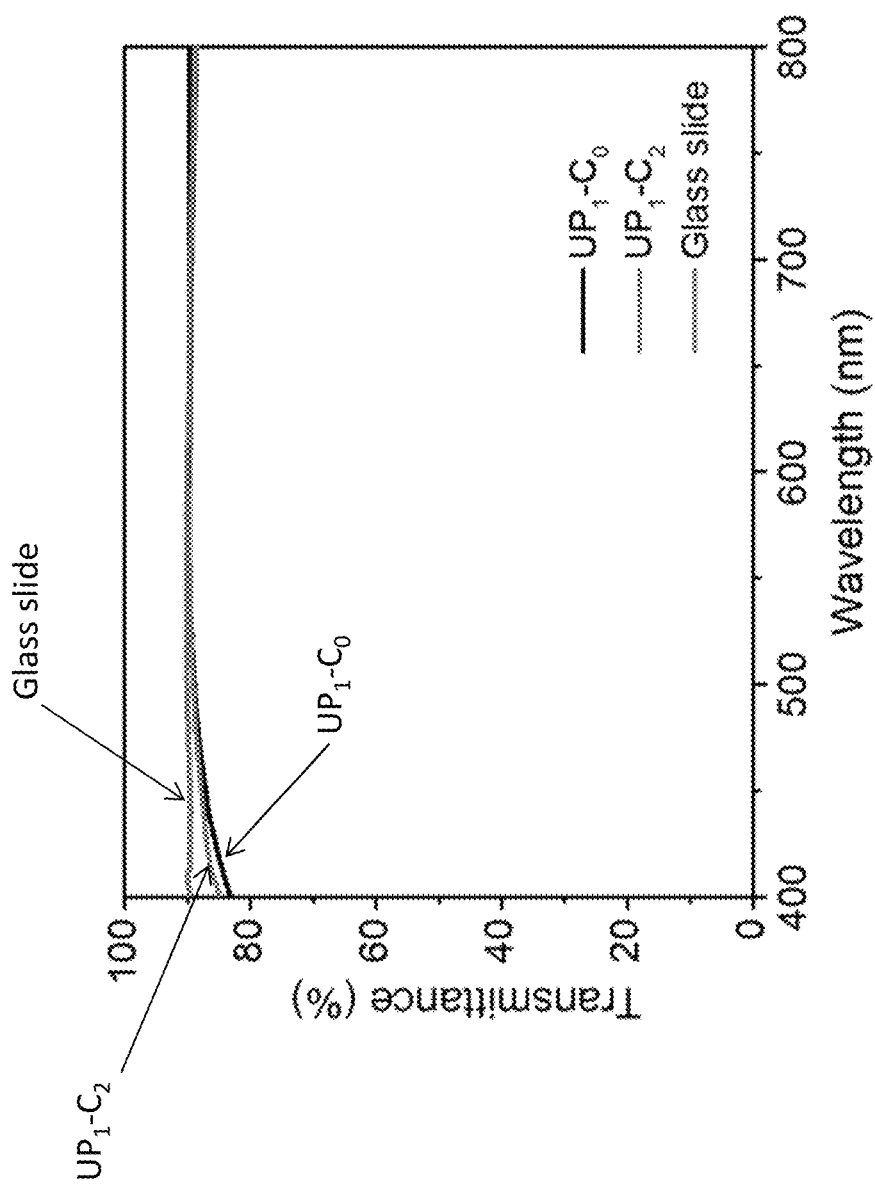
FIG. 11 is a line graph showing transmittance (in %) of the monomeric unit in accordance with an example embodiment.

FIG. 11 is a line graph showing samples of the composition with two different amounts of hydrophobic material, i.e. $UP_1$-$C_0$ and $UP_1$-$C_2$, display good transmittance as high as 90% in the visible region.

The results advantageously show that varying the content of hydrophobic material in the composition can be used to alter or control the mechanical strength of the composition, and that the composition exhibits self-healing characteristics.

Example 1D

Antimicrobial Analysis

Disk Diffusion Assay

The disk diffusion assay was used to test the antimicrobial ability of the composition. A visible area, known as the zone of inhibition, will become visible around the disk if bacterial growth is being controlled or bacteria are being killed.

Gram-positive *Staphylococcus aureus* (*S. aureus*) and gram-negative *Escherichia coli* (*E. coli*) solution were tested, and were diluted to 0.5 McFarland turbidity standard. A sterile swab was dipped into the diluted bacteria solution and rubbed over the entire surface of LB agar plate. The disks with coatings (10 mg of samples of different weight ratios $UP_1$-$C_0$, $UP_1$-$C_2$, $UP_1$-$C_5$) were put on the center of the LB agar plates after bacteria seeding. These plates were incubated for 24 hours at 37° C. and the photographs of the inhibition zones were recorded by Leica camera.

Figure 7C:
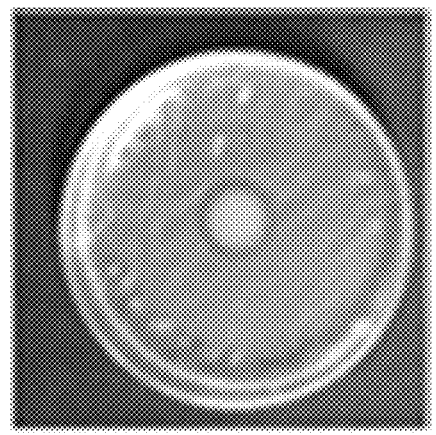
FIG. 7C is a photograph of an agar plate showing the results of an antimicrobial test in the presence of gram-positive bacteria S. aureus.
Figure 7B:
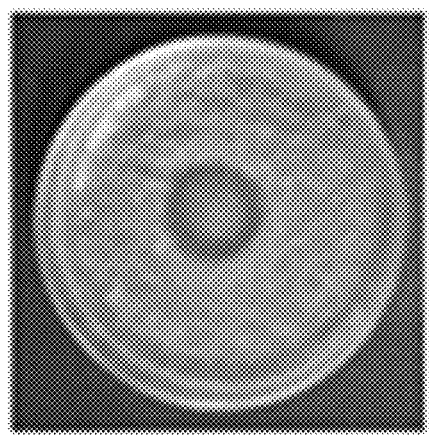
FIG. 7B is a photograph of an agar plate showing the results of an antimicrobial test of the composition in the presence of gram-positive bacteria S. aureus.
Figure 7A:
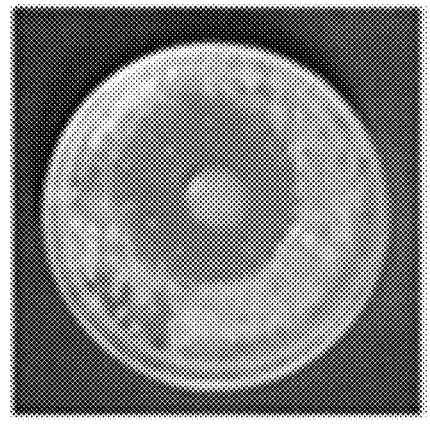
FIG. 7A is a photograph of an agar plate showing the results of an antimicrobial test of the composition in the presence of gram-positive bacteria S. aureus.
Figure 7F:
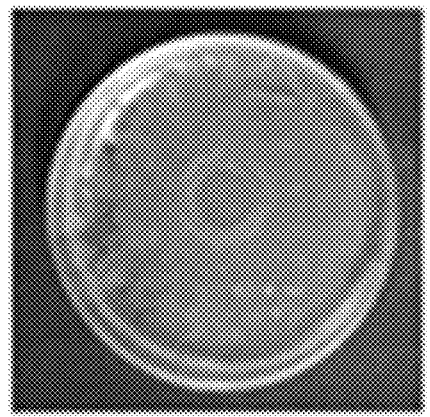
FIG. 7F is a photograph of an agar plate showing the results of an antimicrobial test in the presence of gram-negative bacteria E. coli.
Figure 7E:
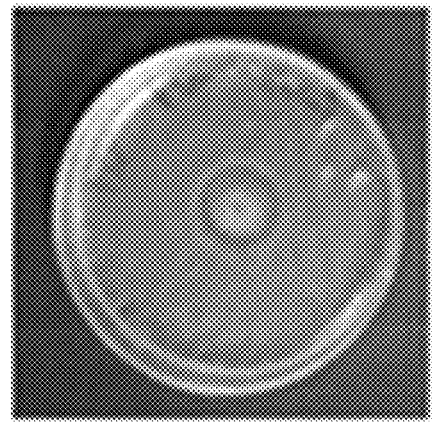
FIG. 7E is a photograph of an agar plate showing the results of an antimicrobial test of the composition in the presence of gram-negative bacteria E. coli.
Figure 7D:
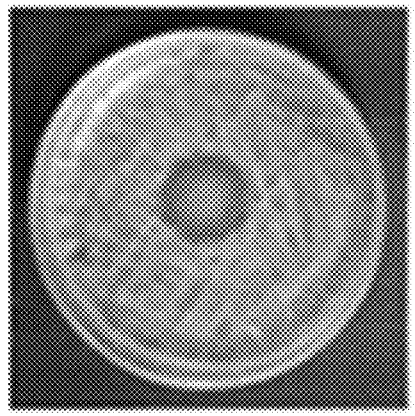
FIG. 7D is a photograph of an agar plate showing the results of an antimicrobial test of the composition in the presence of gram-negative bacteria E. coli.

FIGS. 7A-7C are the results from the antimicrobial test on gram-positive bacteria for $UP_1$-$C_5$, $UP_1$-$C_2$, $UP_1$-$C_0$, respectively. FIGS. 7D-7F are the results from the antimicrobial test on gram-native bacteria for $UP_1$-$C_5$, $UP_1$-$C_2$, $UP_1$-$C_0$, respectively.

Compared to the control sample $UP_1$-$C_0$ (FIG. 7C and FIG. 7F), the composition comprising one or more monomeric units and hydrophobic material, i.e. essential oil in this embodiment, exhibited anti-bacterial ability to gram-positive and gram-negative bacteria. Bactericidal ability of the composition also positively correlated with the content of essential oil in the composition. When FIGS. 7A-7C were compared with FIGS. 7D-7F, samples of the composition at the same concentration appear to have a stronger bactericidal effect on gram-positive bacteria when compared with gram-negative bacteria.

Time Dependent Disinfection Efficiency 1 cm×1 cm glass slides coated with varying amounts of essential oil, particularly carvacrol, $UP_1$-$C_0$, $UP_1$-$C_2$ or $UP_1$-$C_5$ (10 mg of each coating) were immersed in 1 mL S. aureus or E. coli solution in 24 well plates. Every thirty minutes the bacteria solution was mixed by vortex and 100 µL aliquots of the bacteria samples were removed, and used for serial dilution on agar plates. The appropriate numbers of colonies formed were counted and the total amount of bacteria in the solution was calculated. The experiment was performed independently three times.

Figure 8A:
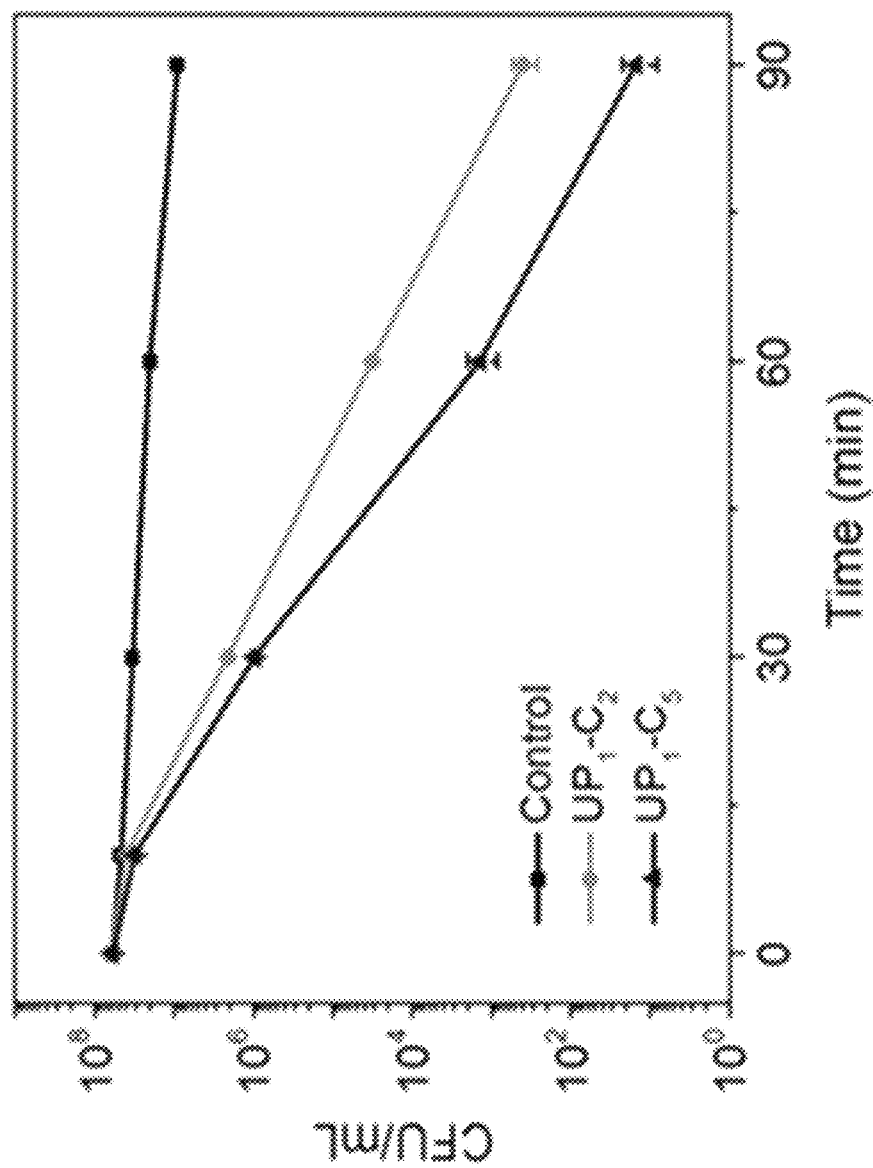
FIG. 8A is a line graph showing time-dependent antimicrobial activity of the composition towards gram-positive bacteria S. aureus.
Figure 8B:
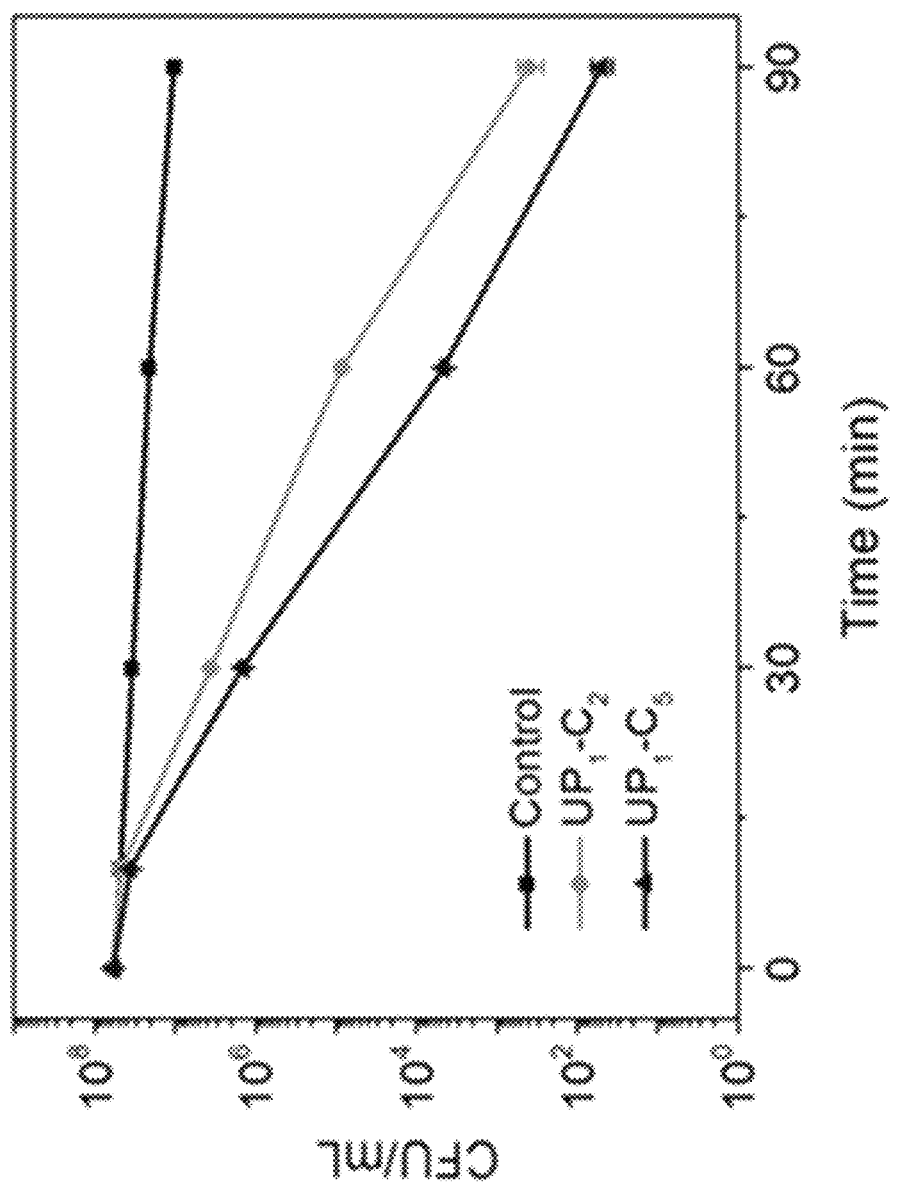
FIG. 8B is a line graph showing time-dependent antimicrobial activity of the composition towards gram-negative bacteria E. coli.

FIG. 8A illustrates time-dependent antimicrobial activity of sample $UP_1$-$C_2$ and $UP_1$-$C_5$ towards S. aureus by analysis of reduction of colony forming units (CFU). FIG. 8B illustrates time-dependent antimicrobial activity of sample $UP_1$-$C_2$ and $UP_1$-$C_5$ towards E. coli by analysis of reduction of CFU. The results illustrated that $UP_1$-$C_2$ and $UP_1$-$C_5$ were able to reduce S. aureus and E. coli colony forming units by more than 5 orders of magnitude after 90 min, corresponding to more than 99.999% reducing efficiency.

These results showed the superior antimicrobial ability of the composition of the present invention.

Example 1E

Release of Carvacrol Encapsulated in Composition in Air or Underwater

Figure 8C:
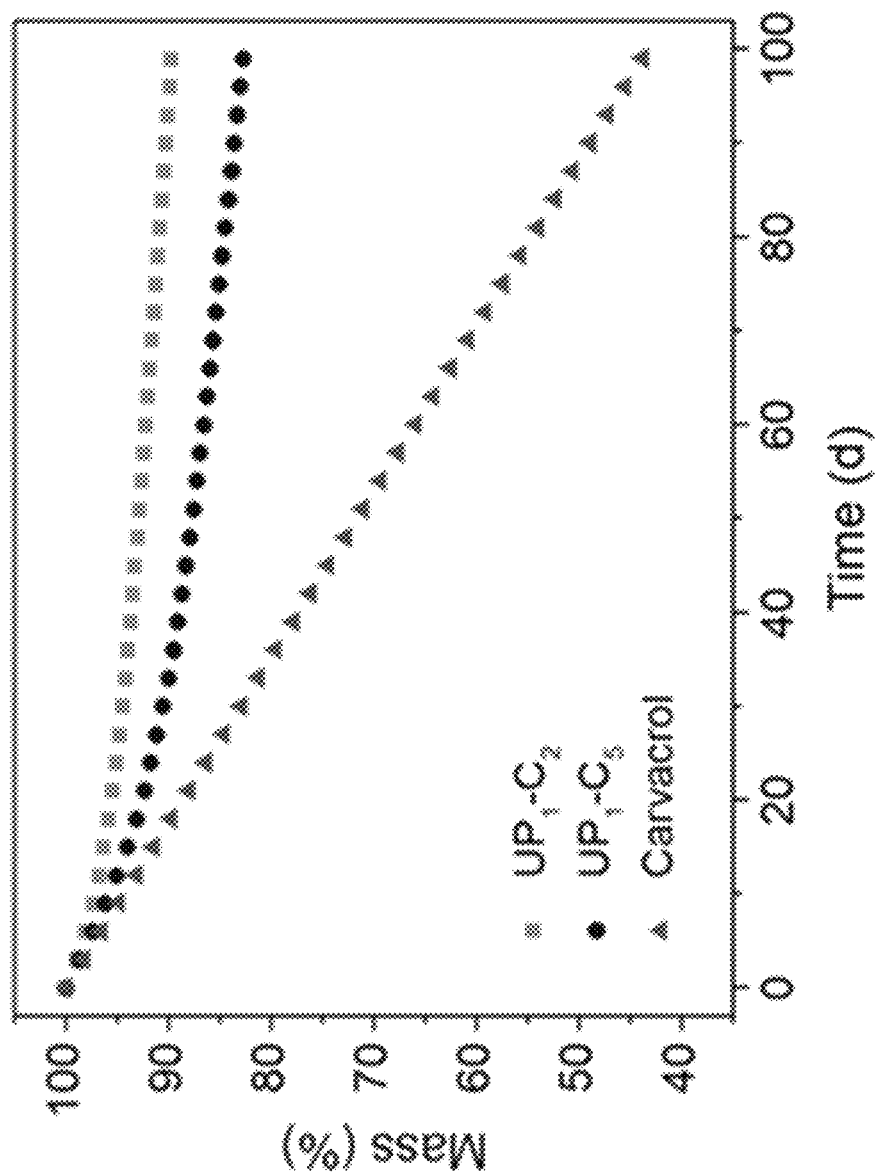
FIG. 8C is a scatter diagram showing the change in mass of the composition and carvacrol over time in accordance with an example embodiment.

The amount of carvacrol, i.e. the hydrophobic material in the composition, released in air was calculated by weight loss and is illustrated in FIG. 8C. The amount of carvacrol released in water was monitored by UV-vis scanning spectrophotometer (Shimadzu 1700), wherein UV main peak absorption of carvacrol can be determined at 275 nm, and is illustrated in FIG. 8D.

With reference to FIG. 8C, in comparison with pure carvacrol, the release amount of carvacrol from composition samples $UP_1$-$C_2$ and $UP_1$-$C_5$ was found to be much lower over 100 days, suggesting long-term stability of the composition in air.

Figure 8D:
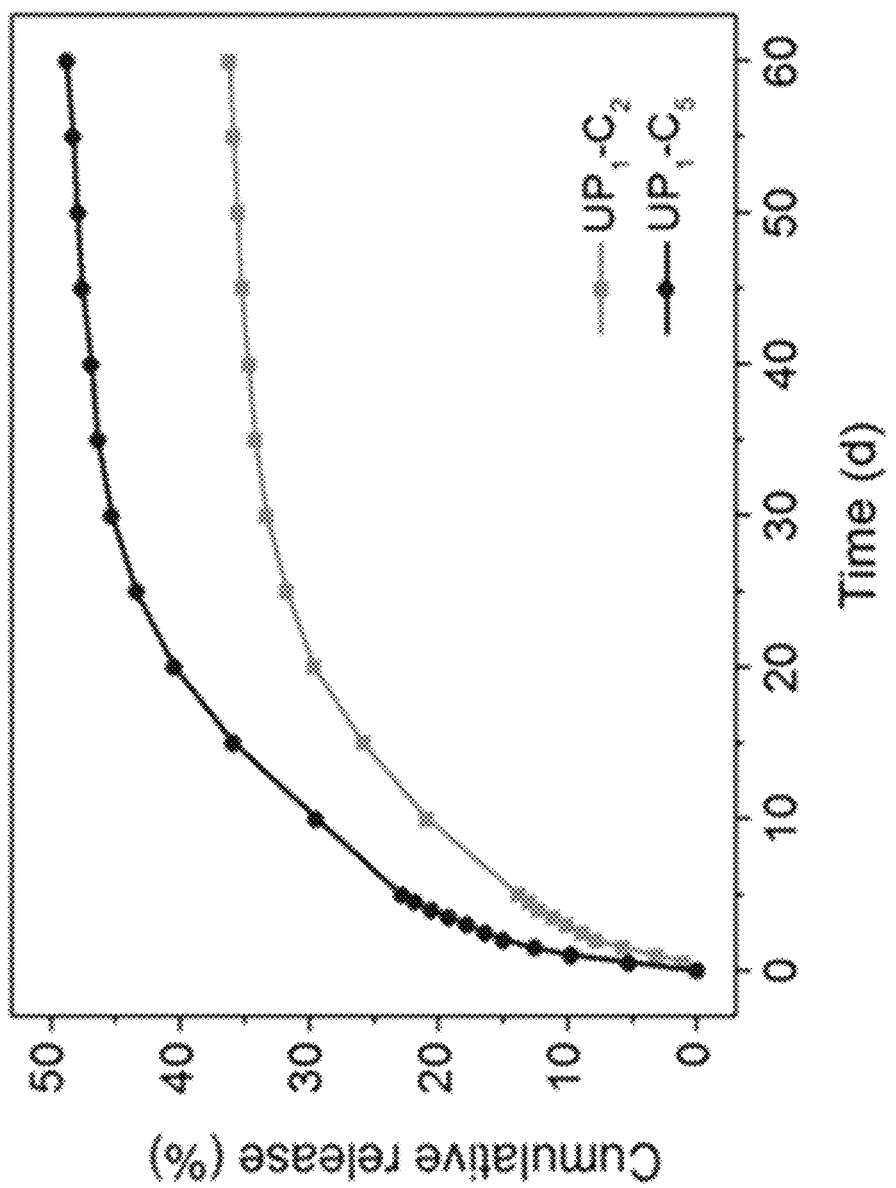
FIG. 8D is a line graph showing the cumulative release of carvacrol from the composition in water over time in accordance with an example embodiment.

The release of the carvacrol encapsulated into the composition was also investigated in water, as shown in FIG. 8D. The cumulative release of carvacrol from the composition samples could last for up to 60 days, demonstrating controlled or sustained release properties of carvacrol when encapsulated into the composition samples. This may be attributed to the strong noncovalent interactions between carvacrol oil and the one or more monomeric units. Thus, the composition of the present invention shows strong prolonged release behavior this providing a highly advantageous composition with wide applicability, such as in the preparation of sustained release dosage forms for various medical purposes.

The present invention provides a multifunctional composition comprising one or more monomeric units encapsulated with a hydrophobic material, such as an essential oil. The composition has been shown to display mechanical robustness, fast healing, strong adhesiveness and sustained release antibiotic properties. Based on the supramolecular polymerization and polymer chains crosslinked networks, hierarchical hydrogen-bond interactions enable high mechanical strength and fast healing at elevated temperatures. Specifically, strong quadruple hydrogen bonds enable the polymerization of monomeric units, and weak intermolecular hydrogen bond contribute to the crosslinks and aggregations of the monomeric units. Carvacrol oil has been shown to readily affect the mechanical strength of the composition through damage to the intermolecular weak hydrogen bonding. Consequently, mechanical and healable properties of the composition can be controlled, thereby beneficially providing a high strength, self-healing, prolonged release composition with antimicrobial properties.

The invention claimed is:

1. A composition comprising:
   a) a supramolecular polymer comprising a plurality of monomeric units, wherein each monomeric unit of the plurality of monomeric units has a structure according to Formula (I):

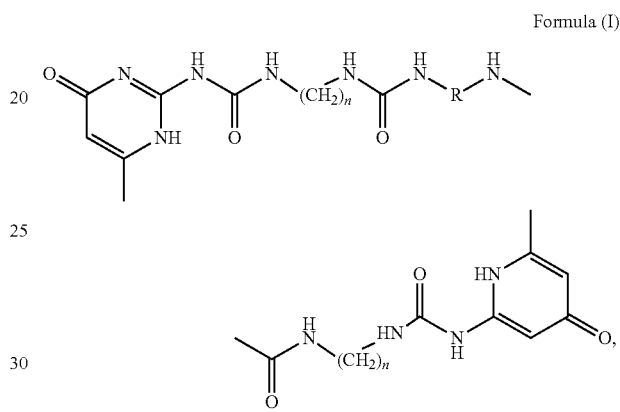

Formula (I)

wherein:
   n is an integer selected from 1 to 10;
   R represents a substituted or unsubstituted cyclic group; and
   b) a hydrophobic material, wherein the hydrophobic material is encapsulated with the supramolecular polymer.

2. The composition of claim 1, wherein the substituted or unsubstituted cyclic group comprises a 4, 5, 6, 7 or 8 membered aryl or heteroaryl group.

3. The composition of claim 1, wherein R has a structure according to Formula (IIa):

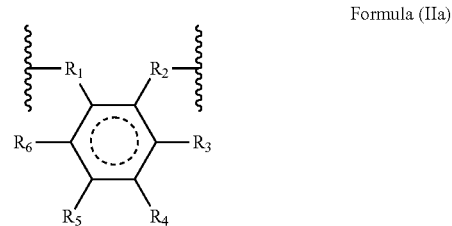

Formula (IIa)

wherein:
   $R_1$ and $R_2$ are independently selected from the group consisting of a linear or branched alkyl group, optionally comprising a heteroatom; a linear or branched alkenyl group, optionally comprising a heteroatom; a linear or branched alkynyl group, optionally comprising a heteroatom; a cycloalkyl group optionally comprising a heteroatom; an aryl group, optionally comprising a heteroatom; and a heteroatom;

$R_3$, $R_4$, $R_5$ and $R_6$ are independently selected from the group consisting of a linear or branched alkyl group, optionally comprising a heteroatom; a linear or branched alkenyl group, optionally comprising a heteroatom; a linear or branched alkynyl group, optionally comprising a heteroatom; a cycloalkyl group, optionally comprising a heteroatom; an aryl group, optionally comprising a heteroatom; a heteroatom; and a hydrogen atom; and wherein the dotted line denotes no double bonds, one double bond, two double bonds, or three double bonds in the cyclic group.

4. The composition of claim 1, wherein R has a structure according to Formula (IIb):

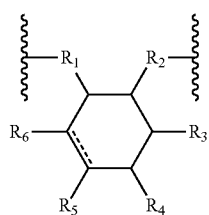

Formula (IIb)

wherein:
- $R_1$ and $R_2$ are independently selected from the group consisting of a linear or branched alkyl group, optionally comprising a heteroatom; and a cycloalkyl group, optionally comprising a heteroatom,
- $R_3$, $R_4$, $R_5$ and $R_6$ are independently selected from the group consisting of a linear or branched alkyl group, optionally comprising a heteroatom, a heteroatom, and a hydrogen atom, and
- the dotted line denotes no double bond or one double bond.

5. The composition of claim 4, wherein $R_1$, $R_2$, $R_3$ and $R_4$ consist of a linear or branched alkyl group, and $R_5$ and $R_6$ consist of a hydrogen atom.

6. The composition of claim 1, wherein each monomeric unit of the plurality of monomeric units has a structure according to Formula (III):

7. The composition of claim 1, wherein the hydrophobic material comprises a liquid.

8. The composition of claim 1, wherein the hydrophobic material comprises an antimicrobial compound.

9. The composition of claim 1, wherein the hydrophobic material comprises an essential oil.

10. The composition of claim 1, wherein the hydrophobic material comprises a compound selected from the group consisting of carvacrol, thymol, p-cymene, limonene, and combinations thereof.

11. The composition of claim 1, wherein the supramolecular polymer comprises a gel and wherein the hydrophobic material is noncovalently-bonded with the plurality of monomeric units.

12. A self-healing, sustained-release antimicrobial coating composition comprising the composition of claim 1, and an antimicrobial compound.

13. The composition of claim 1, wherein the composition has an elastic modulus of at least 50 MPa at 25° C. and of less than 5 MPa at 100° C.

14. A method of killing or controlling the growth of microorganisms comprising contacting the microorganisms with the composition of claim 1.

15. A method of preparing a composition, said method comprising the steps of:

(a) providing a plurality of monomeric units, wherein each monomeric unit of the plurality of monomeric units has a structure of Formula (I):

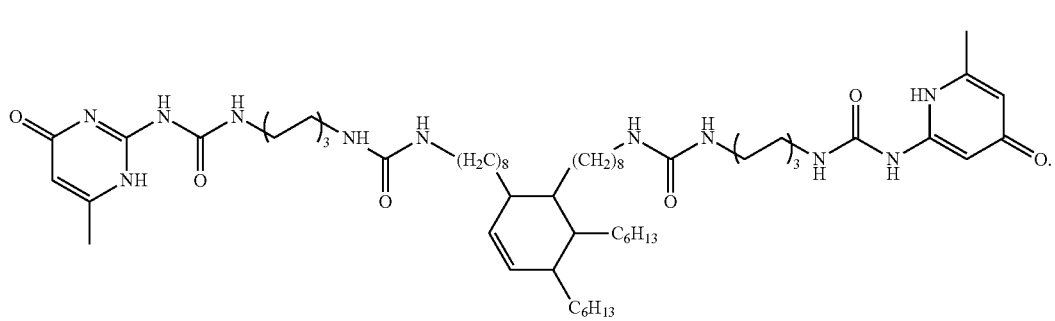

Formula (III)

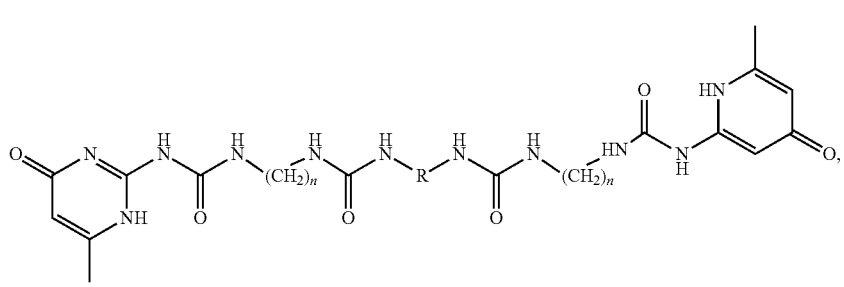

Formula (I)

in which:
n is an integer selected from 1 to 10;
R represents a substituted or unsubstituted cyclic group;
(b) mixing the plurality of monomeric units with a hydrophobic material; and
(c) obtaining a supramolecular polymer comprising the plurality of monomeric units, wherein the hydrophobic material is encapsulated in the supramolecular polymer.

16. The method of claim 15, wherein R of Formula (I) has a structure of Formula (IIa):

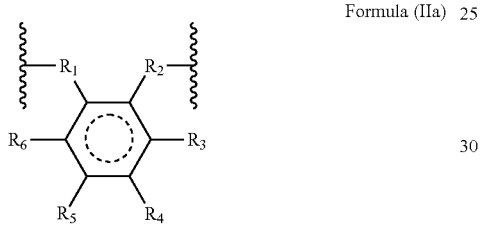

Formula (IIa)

in which:
$R_1$ and $R_2$ are independently selected from the group consisting of a linear or branched alkyl group, optionally comprising a heteroatom; a linear or branched alkenyl group, optionally comprising a heteroatom; a linear or branched alkynyl group, optionally comprising a heteroatom; a cycloalkyl group optionally comprising a heteroatom; an aryl group, optionally comprising a heteroatom; and a heteroatom;

$R_3$, $R_4$, $R_5$ and $R_6$ are independently selected from the group consisting of a linear or branched alkyl group, optionally comprising a heteroatom; a linear or branched alkenyl group, optionally comprising a heteroatom; a linear or branched alkynyl group, optionally comprising a heteroatom; a cycloalkyl group, optionally comprising a heteroatom; an aryl group, optionally comprising a heteroatom; a heteroatom; and a hydrogen atom; and the dotted line denotes no double bonds, one double bond, two double bonds, or three double bonds in the cyclic group.

17. The method of claim 15, wherein R of Formula (I) has a structure of Formula (IIb):

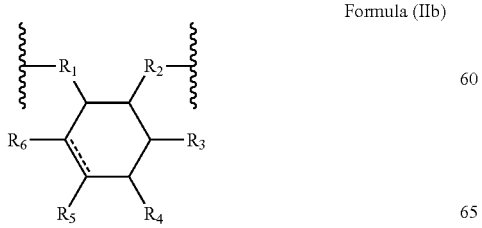

Formula (IIb)

in which:
$R_1$ and $R_2$ are independently selected from the group consisting of a linear or branched alkyl group, optionally comprising a heteroatom; and a cycloalkyl group, optionally comprising a heteroatom;

$R_3$, $R_4$, $R_5$ and $R_6$ are independently selected from the group consisting of a linear or branched alkyl group, optionally comprising a heteroatom; a heteroatom; and a hydrogen atom; and wherein the dotted line denotes no double bond or one double bond.

18. The method of claim 15, wherein the one or more monomeric units of the plurality of monomeric units in the step (a) are prepared by reacting a compound having Formula (IVa) and a compound having Formula (IVb):

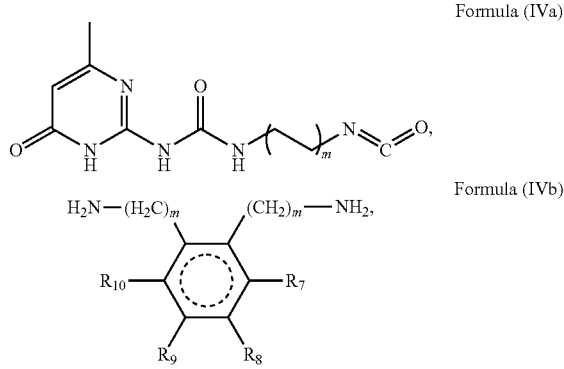

Formula (IVa)

Formula (IVb)

in which:
m is an integer selected from 1 to 10;

$R_7$, $R_8$, $R_9$, $R_{10}$ are independently selected from the group consisting of a linear or branched alkyl group, optionally comprising a heteroatom; a heteroatom; and a hydrogen atom; and wherein the dotted line denotes no double bonds, one double bond, two double bonds, or three double bonds in a cyclic group of Formula (IVb).

19. The method of claim 15, wherein each monomeric unit of the plurality of monomeric units has a structure of Formula (III):

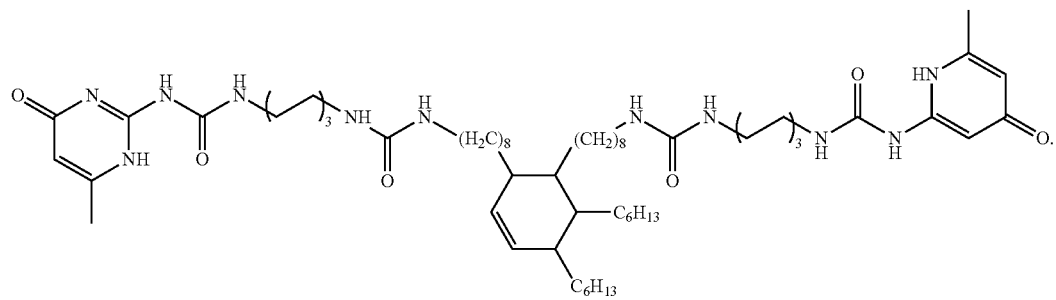

Formula (III)

20. The method of claim 15, wherein the hydrophobic material is a liquid.

21. The method of claim 15, wherein the hydrophobic material is an essential oil.

22. The method of claim 15, wherein the hydrophobic material comprises an antimicrobial compound.

23. The method of claim 15, wherein the hydrophobic material comprises a compound selected from the group consisting of carvacrol, thymol, p-cymene, limonene, and combinations therof.

24. The method of claim 15, wherein step (b) is conducted by dissolving the plurality of monomeric units in the hydrophobic material at a temperature of 50° C. to 150° C.

* * * * *